United States Patent [19]

Kunz

[11] 4,305,722
[45] Dec. 15, 1981

[54] WETTING CYCLE FOR SPUN BLOOD SMEARS

[75] Inventor: Hans J. Kunz, Acton, Mass.

[73] Assignee: Coulter Electronics, Inc., Hialeah, Fla.

[21] Appl. No.: 159,390

[22] Filed: Jun. 13, 1980

[51] Int. Cl.³ .......................... B44D 1/02; G01N 1/28
[52] U.S. Cl. ..................................... 23/230 B; 424/3; 427/2
[58] Field of Search ........................ 23/230 B; 422/57; 427/2, 4; 424/3

[56] References Cited

U.S. PATENT DOCUMENTS

| 3,572,890 | 3/1971 | Adamik | 427/2 X |
| 3,577,267 | 5/1971 | Preston, Jr. et al. | 427/2 |
| 3,705,048 | 12/1972 | Staunton | 427/2 |
| 4,089,989 | 5/1978 | White et al. | 427/2 |
| 4,183,973 | 1/1980 | Beaty et al. | 427/2 |
| 4,209,548 | 6/1980 | Bacus | 427/2 |

Primary Examiner—Ronald Serwin
Attorney, Agent, or Firm—William A. Newton

[57] ABSTRACT

Disclosed is a method of preparing a blood smear on a microscope slide wherein a diluent is applied to the slide, the slide is spun so as to be coated with a thin layer of diluent, a blood sample then is dispensed on the slide, and the slide is spun a second time to spread the blood sample over the slide.

7 Claims, 1 Drawing Figure

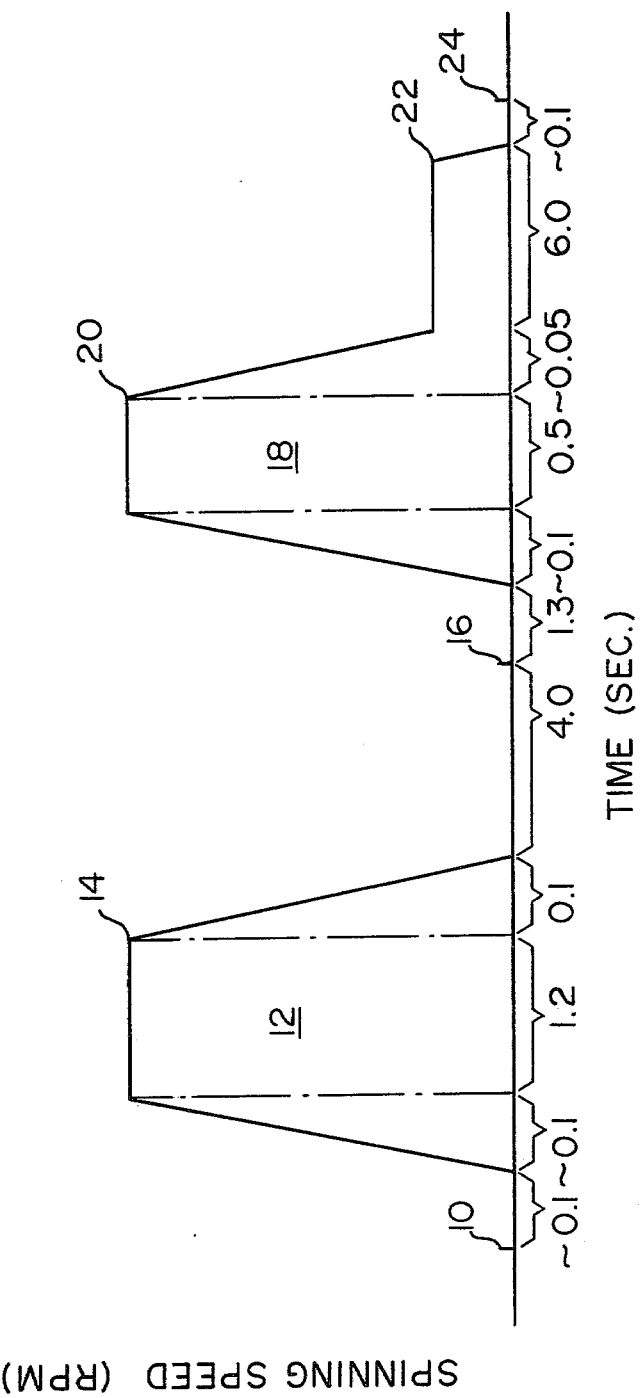

WETTING CYCLE FOR SPUN BLOOD SMEARS

BACKGROUND OF THE INVENTION

1. Field of Invention

The invention generally relates to the preparation of blood films or smears on microscope slides or similar substrates. While applicable to all techniques for evaluation of the resulting smears, the method especially is adapted for use in connection with automated blood cell analysis using computerized pattern recognition systems, commonly known as automated differential analyzers.

2. Description of Prior Art

Monolayers of cells have been prepared by a number of techniques, for example, by wedging, i.e., "push smears", by coverslip techniques and more recently by spinning. The major advantages of the spinning technique are the uniform coverage of at least a major portion of a 1"×3" microscope slide area and the good cell morphology analysis which can be achieved. Especially for automated differential analyzers, these advantages have made spun smears very attractive. The amount of whole blood required for these spun smears is in the range of 100 to 200 microliters per slide, depending on the density of cells per quantity of sample liquid considered adequate, the use of whole blood or diluted blood and also on the amount of blood wasted, for example, blood remaining on the wall of test tubes, in dispensers and in the dilutors. If less fluid is dispensed, only an irregular, star-shaped pattern is obtained, which covers only part of the slide area.

The most frequent use of these blood films is for differential white cell counts and for assessment of the red cell morphology. In normal blood samples there are about 600 erythrocytes (red cells) for every leukocyte (white cell). Hence, in order to find a minimum of 100 leukocytes for a differential count, enough of a slide surface has to be scanned to cover an average of $6 \times 10^4$ erythrocytes. To find these white cells in a reasonable time, of the order of 2 minutes total, one would ideally like to have a blood film with closely spaced, but not touching or overlapping cells, with well defined platelets, few damaged cells, uniform and reproducible cell size for assessment of degrees of microcytosis and macrocytosis, well developed pallor of normal red cells and freedom from artifacts and debris.

Assuming a slide area of 1"×3", normal blood and a distribution, where on the average two red cells are contained in an area of 16 microns by 16 microns, a volume of blood which would contain enough cells to form the above described monolayer can be calculated easily. About 1.5 microliters of whole blood are required for this. If, on the other hand, a blood film containing 1,000 white cells from normal blood is desired, an area of only 76.8 mm² would be needed, constituting, for example, a circle of less than 1 cm diameter on the slide. The whole blood volume required for this would be only about 1.5/25=0.06 microliters. Even if the whole slide is covered, only about 1% of the blood used becomes part of the monolayer, while about 99% is spun off, i.e. 150 microliters versus 1.5 microliters.

If the proper slide preparation method can be found, it is apparent from the above described wastage that spun slides could be prepared with a substantially smaller amount of blood. The amount of blood sample required to prepare a film becomes important especially in the following applications: fingersticks; pediatric sticks; need to prepare multiple slides from the same donor; research applications, using blood from small animals for example; and application of spun layers outside hematology with small sample requirements.

SUMMARY OF THE INVENTION

The invention is directed toward a method of preparing a spun blood smear on a microscope slide or like substrate, wherein a relatively small quantity of either whole or diluted blood can be spread over at least most of the substrate. A coating liquid, for example a diluent, is dispensed on the substrate and then the substrate is spun so that the coating liquid spreads into a thin liquid film over the substrate. Thereafter, the whole or diluted blood is dispensed onto the substrate and the substrate is spun for a second time to spread the blood over the substrate and the thin liquid film.

The method of the invention allows for a small quantity of blood to be spread over a given substrate with the desired density and other parameters of a standard smear, but requires more than one order of magnitude less blood than normally used with standard spun smears. This benefit results from the fact that very little of the blood is spun off during spinning with the method of the invention. This method is extremely useful in the previously described situations wherein only a small sample of blood is available for examination or where it is desirable to obtain only small samples.

DESCRIPTION OF THE DRAWING

Further objects and advantages of the present invention will become apparent as the following description proceeds, taken in conjunction with the accompanying drawing in which:

The sole FIGURE graphically shows the spin sequence utilized to implement the method of the present invention.

DESCRIPTION OF PREFERRED METHOD

A microscope slide is placed in a slide holder of a spinning apparatus for blood film preparation, which may be part of a differential analyzer system, for example as disclosed in U.S. Pat. No. 4,016,828 to Maher, Jr. et al. The slides are typically 1"×3". After the slide is placed in the slide holder, preferably 200 to 300 microliters of, for example, a diluent, is dispensed on the center of the slide. During a wetting spin cycle the slide then is spun, resulting in a thin liquid layer of diluent remaining on the slide. Preferably with a minimal amount of delay, premeasured amounts of blood and diluent are positioned on the slide. During a second spin cycle, the slide is spun again. In conventional manner, the slide is taken out, allowed to air dry, fixed, stained and evaluated.

Referring to the sole FIGURE, an illustrative graph of spinning speed versus time demonstrates the spin sequence for implementing the above described method on the spinning apparatus, such as previously mentioned apparatus for blood film preparation of U.S. Pat. No. 4,016,828. The diluent for forming the thin layer is dispensed on the slide by the time indicated by numeral 10. The diluent can be, for example, a saline solution. One suitable saline solution is sold under the trademark DIFF3 ® diluent, and has 9.9 grams per liter of NaCl so as to provide a proper osmotic balance for the cells. Although the use of a diluent is preferred, other coating liquids can be used. During the wetting spin cycle, generally referred to by numeral 12, the diluent is spread over most of or all of the slide area to give the slide the initial thin liquid film. During the wetting spin cycle, the spinning apparatus is operated at, for example, 3,500 RPM's, as indicated by numeral 14.

By the time indicated by numeral 16, the blood or blood and diluent has been dispensed. Two examples of slide preparation for this step of the method would be the direct depositing of whole blood, about 20 microliters; and the depositing of a blood/diluent (1:1) mixture from a capillary pipette. It has been determined that the resulting slide is still rather dense, in the first example, so that the lower limit of the method can be below 10 microliters of blood for a slide, with the mean cell density still being comparable to a standard slide which uses about 200 microliters of blood per slide; some of which remains in the diluter and is rinsed out subsequently. Also, the pipette used could be coated with an anti-coagulant or the anti-coagulant could be added to the blood diluent. Blood and diluent have, in this case, to be mixed, for example, 10 microliters of blood and 10 microliters of anti-coagulated diluent in a 20 microliter pipette. Small wire magnets are available, or a piston type mixer could be used for mixing in a conventional manner.

The slide is spun again during a spin cycle, generally indicated by numeral 18, during which the spinning apparatus is operated, for example, at speeds of 3,200 to 3,500 RPM's for diluted blood, as indicated by numeral 20. The spinning apparatus, toward the end of the spin cycle 18, is operated, for example, at 1,000 to 1,500 RPM's, as shown by numeral 22. At the time indicated by numeral 24, the slide is taken out and the spin processing is complete.

It has been determined that it is possible to achieve with about 10 microliters or less of blood a distribution on the slide which is comparable in density and other parameters with a standard spun smear, but requiring more than one order of magnitude less blood. Spun smears of good quality can be made according to this invention with less blood than is required for conventional wedged smears. It appears also, that a differential count can be made on as little a blood sample as 3 microliters, if one does not require that substantially the whole slide area is covered. A generally circular area around the slide center can be covered and has to be scanned in this case.

The method can also be extended to include the reticulocyte process. For the retic preparation, blood would not be mixed with diluent, but with reticulocyte stain. Incubation time of (10±1) minutes for example would be allowed and then the blood film prepared in a similar manner to that as described earlier.

Although particular embodiments of the invention have been shown and described here, there is no intention to thereby limit the invention to the details of such embodiments. On the contrary, the intention is to cover all modifications, alternatives, embodiments, usages and equivalents of the subject invention as fall within the spirit and scope of the invention, specification and the appended claims.

What is claimed is:

1. A method of preparing a blood smear on a microscope substrate, said method comprising:
    dispensing a coating liquid on the substrate;
    thereafter, spinning the substrate about an axis substantially perpendicular to the plane of the substrate so that the coating liquid spreads into a relatively thin layer over at least a portion of the substrate;
    thereafter, dispensing a quantity of blood onto the liquid coated substrate;
    thereafter, spinning the substrate for a second time so that the blood spreads over at least a portion of the liquid coated substrate.

2. The method of claim 1 wherein said step of dispensing the coating liquid comprises dispensing a diluent for blood.

3. The method of claim 1 wherein said step of dispensing a quantity of blood comprises dispensing whole blood.

4. The method of claim 1 wherein said step of dispensing a quantity of blood comprises dispensing diluted blood.

5. A method of preconditioning a substrate for a blood smear, said method comprising the steps of:
    applying a blood cell free liquid to the substrate, and then
    spinning the substrate about the axis substantially perpendicular to the plane of the substrate to cause the liquid to spread into a relatively thin layer over at least a portion of the substrate.

6. The method of claim 5 in which the blood cell free liquid is a blood diluent.

7. The method of claim 5 in which said spinning is for approximately one second at approximately 3,500 RPM.

* * * * *